(12) United States Patent
Zahn et al.

(10) Patent No.: US 7,241,904 B2
(45) Date of Patent: Jul. 10, 2007

(54) PENTAFLUOROSULFANYL-SUBSTITUTED THIENOTHIOPHENE MONOMERS AND CONDUCTING POLYMERS

(75) Inventors: Steffen Zahn, Pennsburg, PA (US); Andrew Francis Nordquist, Whitehall, PA (US); Kristen Elaine Minnich, Allentown, PA (US); Guari Sankar Lal, Whitehall, PA (US); William Franklin Burgoyne, Jr., Bethlehem, PA (US); Axel Klauck-Jacobs, Whitehall, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/439,553

(22) Filed: May 23, 2006

(65) Prior Publication Data

US 2006/0208233 A1 Sep. 21, 2006

Related U.S. Application Data

(63) Continuation of application No. 11/229,516, filed on Sep. 20, 2005, now Pat. No. 7,060,846, which is a continuation-in-part of application No. 10/958,054, filed on Oct. 4, 2004, now Pat. No. 7,094,365.

(51) Int. Cl.
*C07D 333/04* (2006.01)
(52) U.S. Cl. ...................................... 549/80
(58) Field of Classification Search ............... 549/29, 549/78, 80; 252/500
See application file for complete search history.

(56) References Cited

U.S. PATENT DOCUMENTS

| | | | |
|---|---|---|---|
| 4,639,328 A | 1/1987 | Krause et al. | |
| 4,659,503 A | 4/1987 | Eidenschink et al. | |
| 4,826,829 A * | 5/1989 | Eurkart et al. ............... | 514/95 |
| 5,055,223 A | 10/1991 | Reiffenrath et al. | |
| 5,300,575 A | 4/1994 | Jonas et al. | |
| 5,892,244 A | 4/1999 | Tanaka et al. | |
| 5,998,804 A | 12/1999 | Suk et al. | |
| 6,585,914 B2 | 7/2003 | Marks et al. | |
| 6,645,401 B2 | 11/2003 | Giles et al. | |
| 6,676,857 B2 | 1/2004 | Heeney et al. | |
| 6,695,978 B2 | 2/2004 | Worrall et al. | |
| 6,709,808 B2 | 3/2004 | Lelental et al. | |
| 6,818,260 B2 | 11/2004 | Farrand et al. | |
| 2003/0085381 A1 | 5/2003 | Worrall et al. | |
| 2003/0216476 A1 | 11/2003 | Kleemann | |
| 2004/0010115 A1 | 1/2004 | Sotzing | |
| 2004/0051084 A1 | 3/2004 | Wessling et al. | |
| 2004/0074779 A1 | 4/2004 | Sotzing | |

FOREIGN PATENT DOCUMENTS

JP 03038588 2/1991
WO WO 00/79617 12/2000

OTHER PUBLICATIONS

U.S. Appl. No. 10/958,054, filed Oct. 4, 2004, Zahn et al.
U.S. Appl. No. 10/958,068, filed Oct. 4, 2004, Nordquist et al.
Neef, et al., "Synthesis and Electronic Properties of Poly (2-phenylthieno [3,4-b]thiophene): A New Low Band Gap Polymer", Chem. Matter. 1999, 11, p. 1957-1958.
Pomerantz et al "Poly(2-decylthieno[3,4b]thiophene). A New Soluble Low-Bandgap Conducting Polymer", Sythetic Metals 84 (1997), p. 243-244.
Winter et al. "New acrylate systems; derivatives of B-SF5-acrylic acid"; Journal of Fluorine Chemistry; 125 (2004) p. 37-41.
LeClerc et al, Structural analysis of Poly(3-alkylthiophene)s; Makromol Chem. 190, (1989); p. 3105-3116.
European Search Report dated Dec. 30, 2005.
Neff, et al; "Synthesis and Electronic Properties of Poly (2-phenylthieno (3,4-b)thiophene): A New Low Band Gap Polymer"; Chem. Matter, 11, 1; pp. 1957-1958; 1999.
Pomerantz, et al; Poly(2-decylthieno (3-4-b)thiophene). A New Soluble Low-Bandgap Conducting Polymer; Synthetic Metals; vol. 84, No. 1-3 (11 ref.); pp. 243-244; 1997.
Pomeantz, et al; "Poly(2-decylthieno(3-4-b)thiopene-4,6-diyl). A New Low Band Gap Conducting Polymer"; Macromolecules, 34 (6); pp. 1817-1822; 2001.

* cited by examiner

*Primary Examiner*—Mark Kopec
(74) *Attorney, Agent, or Firm*—Michael K. Boyer

(57) ABSTRACT

Disclosed are monomers of the formula:

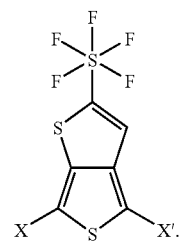

4 Claims, No Drawings

PENTAFLUOROSULFANYL-SUBSTITUTED THIENOTHIOPHENE MONOMERS AND CONDUCTING POLYMERS

This application is a CON of Ser. No. 11/229,516 (filed Sep. 20, 2005, now U.S. Pat. No. 7,060,846, which application is a CIP of Ser. No. 10/958,054 (filed Oct. 4, 2004, now U.S. Pat. No. 7,094,365).

BACKGROUND OF THE INVENTION

Electrically conducting polymers have developed into a material of choice for a variety of organic optoelectronics applications. Such applications for optoelectronics include polymeric light emitting diodes (thin film displays), solid state lighting, organic photovolatics, advanced memory devices, organic field effect transistors, ultracapacitors and electroluminescent devices.

One of the first of many electrically conducting polymers was polyacetylene and the discovery of conductivity in such polymer created substantial interest in other types of electrically conducting polymers. Recently, conjugated poly (thiophenes) and substituted thiophene derivatives have been discovered to have electrically conducting properties. A feature of these polymers is that they can be cast into films and doped with conventional p- and n-type dopants or the doped polymers can be cast into films and their electrical properties modified accordingly, thereby lending themselves suitable for use in a variety of optoelectronic applications.

Representative articles and patents illustrating thiophene monomers and electrically conducting polymers including thiophene and derivatives thereof are as follows:

U.S. Pat. No. 6,645,401 discloses conjugated polymers of dithienothiophene (DTT) with vinylene or acetylene connecting groups as suitable for producing semiconductors or charge transport materials useful in electrooptical and electronic devices including field effect transistors, photovoltaic, and sensor devices. Polymers containing DTT formed by electrochemical polymerization were known but had limitations in terms of solubility and photovoltaic properties.

U.S. Pat. No. 6,585,914 discloses fluorocarbon-functionalized and/or heterocyclic modified poly(thiophenes) such as α, ω-diperfluorohexylsexithiophene for use in forming films which behave as n-type semiconductor. These poly (thiophenes) also can be used to form thin film transistors with FET (Field effect transistor) mobility.

U.S. Pat. No. 6,676,857 discloses polymers having polymerized units of 3-substituted-4-fluorothiophene as liquid crystal materials for use in semiconductors, charge transport materials, electrooptical field effect transistors photovoltaic and sensor devices.

U.S. Pat. No. 6,695,978 discloses polymers of benzo[b] thiophene and bisbenzo[b]thiophene and their use as semiconductors and as charge transport materials in electrooptical devices.

U.S. Pat. No. 6,709,808 discloses image forming materials incorporating electrically conductive polymers based upon pyrrole-containing thiophene polymers and aniline containing polymers.

U.S. 2004/00010115A1 discloses homopolymers and copolymers comprised of repeating units of thieno[3,4-b] thiophene for use in electroactive applications. Copolymers can be formed with 3,4-ethylendioxythiophene, dithiophene, pyrrole, benzothiophene monomers, and the like.

The article, *Synthesis and Electronic Properties of Poly (2-phenyl-thieno[3,4-b]thiophene)*: A new Low Band Gap Polymer, Chem. Mater. 1999, 11, 1957–1958 discloses various thienothiophene polymers including poly(2-phenyl thieno[3,4-b]thiophene) and poly(2-decyl thieno[3,4-b]-thiophene) as conducting polymers.

The article, *Poly(2-decyl thieno[3,4-b]thiophene): a New Soluble Low-Band gap Conducting Polymer*, Synthetic Metals 84 (1997) 243–244 discloses various polymeric thienothiophenes including poly(2-decyl thieno[3,4-b] thiophene) and a process for preparing the polymer.

The disclosure of the previously identified patents, patent applications and articles is hereby incorporated by reference.

BRIEF SUMMARY OF THE INVENTION

The invention relates to thienothiophene monomers having an $SF_5$ group and to conducting oligomers and polymers formed by the polymerization of such monomers (polymerized units) and their use as hole injection materials, charge transport materials, or as semiconductors, in optical, electrooptical or electronic devices, polymeric light emitting diodes (PLED), organic field effect transistors (FET or OFET), flat panel display applications (i.e. LCD's), radio frequency identification (RFID) tags, ultracapacitors, organic photovoltaics (OPV's), sensors, in small molecule or polymer based memory devices, electrolytic capacitors and as a hydrogen storage material.

Light emitting polymers (PLED) require a hole injecting layer (HIL). The purpose of the HIL is to transmit the holes from the ITO (Anode) to the light emitting material. The efficiency of this transmission process is dependant on the differences of the workfunctions of the materials involved. The workfunction of the HIL material should match or be below the workfunction of the light emitting material. For example, if the workfunction of the polymeric light emitting material is −5.5 eV, then the workfunction of −5.5 eV or less for the HIL is desired for an efficient device. Desirable polymeric light emitting materials for use in PLED's exhibit a range of workfunctions between −5.2—−5.7 eV. The inventive Poly(2-pentafluorosulfanyl-thieno[3,4-b]thiophene) can meet this workfunction range.

Advantages can be achieved by using the monomers and polymers based upon $SF_5$ substituted thienothiophenes and derivatives thereof. The advantages provided by some of the monomers and polymers of this invention may include one or more of the following: conducting polymers having low negative workfunction values making them suited as hole injecting materials; conducting polymers having low band gap values making them suitable transparent conductors; conducting polymers useful in a wide range of electronic applications; and hole injection material having a matched workfunction levels between the hole injection material and the light emitting layer.

DETAILED DESCRIPTION OF THE INVENTION

This invention relates to compositions of matter based upon the monomer, 2-pentafluorosulfanyl-thieno[3,4-b] thiophene, its derivatives, and to conjugated oligomers and polymers comprised of multiple units of the respective monomers.

One aspect of the invention relates to compositions of matter represented by formula A:

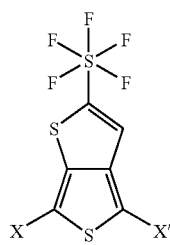

A where X and X' are independently selected from the group comprising H, halogen atoms, MgCl, MgBr, MgI, Sn(R')$_3$, where R' comprises C$_{1-6}$ alkyl or —OC$_{1-6}$ alkyl, boronic acids, boronic esters, —CH=CHR" where R" comprises H or C$_{1-6}$ alkyl, —OC$_{1-6}$ alkyl, —COOC$_{1-6}$ alkyl, —S—COR'", —COR'" where R'" comprises H or C$_{1-6}$ alkyl, —C≡CH, and polymerizable aromatic groups, such as phenyl, naphthalene, pyrrole, dithiophene, thienothiophene, thiophene and so forth. Examples of halogen atoms comprise F, Cl, Br, and I.

One useful monomer for producing homopolymers and copolymers comprises one where X and X' are H and represented by the formula B:

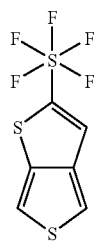

B

Electrically conducting oligomers and polymers comprised of polymerized units of substituted 2-pentafluorosulfanyl-thieno[3,4-b]thiophene are another aspect of the invention and are represented by formula C:

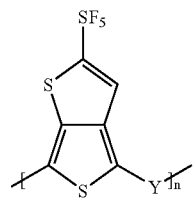

C where n is an integer, Y comprises —CZ$^1$=CZ$^2$- or —C≡C—, and Z$^1$ and Z$^2$ are independently H, F, Cl or CN. Oligomers often have from about 2 to 10 units may be used, for example, to produce memory and field effect transistor devices. Polymers having from about 11 to about 50,000 units, often from about 20 to about 10,000 units may be useful in preparing films as hole injection materials in various electrooptical applications.

Useful homopolymers are represented by the formula D:

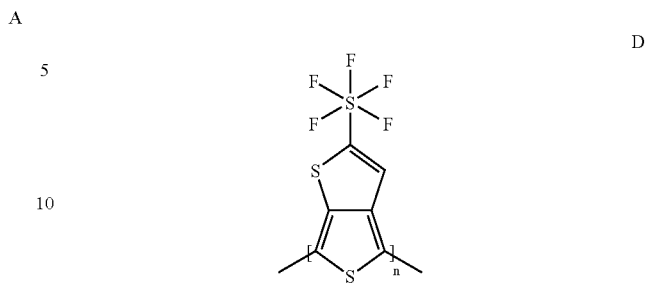

D where n is an integer as represented above.

The monomer of formula A where X and X' are H can be synthesized by the representative 5 step reaction scheme as follows:

Step 1:

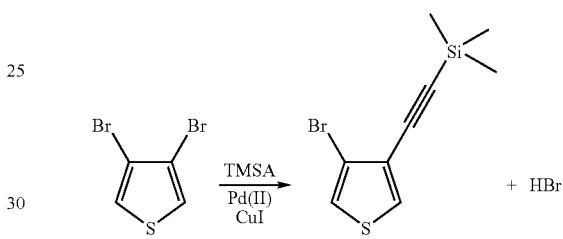

This generally equal molar reaction with trimethylsilacetylene (TMSA) can be carried out while in the presence of a suitable catalyst and in a substantially anhydrous environment, or in a substantially anhydrous environment comprising at least one hydrocarbon (e.g., toluene) with at least one amine such as diethylamine or any other suitable organic secondary or tertiary amine. By "substantially anhydrous environment" it is meant that less than about 1 wt. % water is present in the reaction. When the reaction is conducted in the presence of at least one amine, the amount of amine will normally range from about 5 to about 30 wt. %. This reaction is normally conducted in an inert atmosphere such as nitrogen or argon This reaction can be conducted at a temperature ranging from about 30C up to about the boiling point of any one of the ingredients.

Step 2:

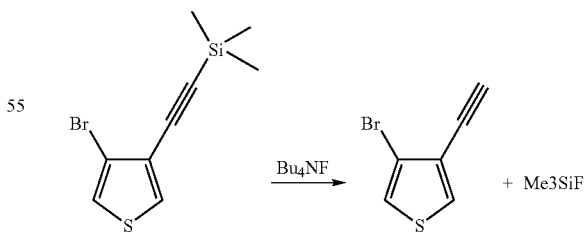

This reaction with an excess amount of tetrabutylammoniumfluoride can be conducted in the presence of any suitable solvent and normally in a basic environment (e.g., a pH of more than about 7.0). Suitable solvents comprise at least one member selected from the group consisting of ethers, halocarbons, hydrocarbons, alcohols, and esters. The amount of solvent ranges from about 5 to about 40 wt.%. The reaction is normally carried out at a temperature ranging from ambient temperature to about −78C (e.g., about −5° C.; depending upon the boiling point of the solvent. A relatively high temperature will usually result in reduced product formation. Besides Bu$_4$NF inorganic bases such as KOH and NaOH in a alcohol or water mixture may be used for removing the protecting group.

Step 3:

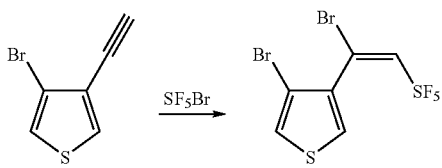

This reaction with SF5Br while in the presence of at least on catalyst such as KF can be conducted in any suitable solvent. The amount of SF5Br will normally be equal molar up to about 10 wt. % excess. Examples of suitable solvents comprise at least one member selected from the group consisting of hydrocarbons, ethers, halocarbons, and other non-protic solvents. The amount of solvent will normally be about 1 to about 20 wt. %. This reaction is normally conducted in the presence of at least one inert gasssuch as nitrogen and argon. The reaction can be conducted at ambient pressure and in a wide temperature range from about −78° C. up to boiling point of solvent.

Step 4:

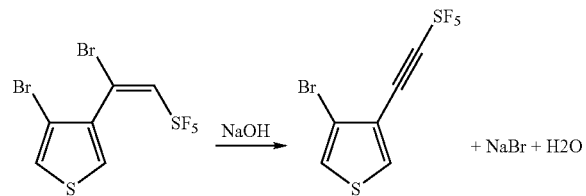

This reaction with sodium hydroxide is normally conducted in the presence of a suitable solvent. Suitable solvents comprise at least one member seleted from the group consisting of hydrocarbons, ethers, halocarbons, alcohols and water. The amount of solvent range range from about 1 to about 20 wt. %. The reaction is conducted with an excess of sodium hydroxide (e.g., up to about 10 times molar ratio). The reaction proceeds in a temperature ranging from about −78° C. up to about the boiling point of solvent.

Step 5:

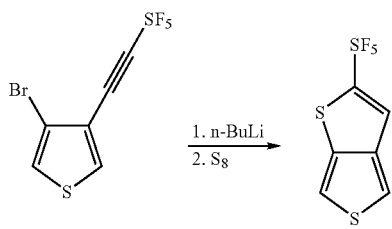

This reaction with buthyllithium or sulfur (e.g., sulfur powder), proceeds readily in solvents lacking acidic protons such as ethers and hydrocarbons (e.g., 1–3 molar hexane), and is normally conducted in an inert atmosphere with inert gases such as nitrogen or argon. Buthyllithium is normally used in about equal molar amounts whereas sulfur is typically used in about 1 to about 10% molar excess. The reaction environment is also normally substantially free of water. Lithiation is normally conducted at relatively low temperatures (e.g., the reaction involving n-BuLi is normally conducted at a temperature less than about −60° C. and usually less than about −78° C.).

Many of the derivatives of the respective monomers where X and X' are other than H are formed post formation of the monomers. In post reaction one or both hydrogen atoms may be replaced with other functional groups. Alternatively, some of the derivatives may be formed, ab initio, by converting thiophene to the derivative and then undergoing the 5 step reaction procedure where the X and X' are compatible with the chemistries outlined in steps 1–5.

Polymerization of 2-pentafluorosulfanyl-thieno[3,4-b]thiophene monomers can be effected utilizing an aqueous phase polymerization method wherein the monomer 2-pentafluorosulfanyl-thieno[3,4-b]thiophene, at least one polyanion and at least one oxidant are reacted in the presence of water under reaction conditions sufficient to form the homopolymer, e.g., poly(2-pentafluorosulfanyl-thieno[3,4-b]thiophene). By this polymerization process, the resulting polymer may be polymerized and doped in a single step.

The amount of polyanion and oxidant to be employed in the aqueous polymerization method may broadly vary and can be determined for any given polymerization without undue experimentation. For example the weight ratio of thieno[3,4-b]thiophene monomer to a desired polyanion typically ranges from about 0.001 to about 50, usually about 0.05 to about 2.0. The mole ratio of thieno[3,4-b]thiophene monomer to a desired oxidant typically ranges from about 0.01 to about 10 usually 0.1 to 2.5. In the case of ferric sulfate, the amount used ranges from about 0.1 to about 5 of thieno[3,4-b]thiophene. The nature of the oxidant may be varied in order to address variants in the ionization potential of the utilized monomers. Various Fe(II)/Fe(III) couplets are known that display different potential depending on their respective ligands (e.g., FeCl$_3$; Fe$_2$(S$_2$O$_8$)$_3$; Fe(phen)$_3$). If weaker oxidants are desired Cu based couplets may be considered. If stronger oxidants are employed Co based couplets should be considered.

Relatively strong oxidants can be employed in the polymerization process. Persulfates and iron (III) salts of organic acids and inorganic acids containing organic residues are useful because they are relatively non-corrosive. While any suitable oxidant can be employed, examples of iron (III) salts of organic acids comprise the Fe(III) salts of C$_{1-30}$ alkyl sulfonic acids, such as methane or dodecane sulfonic acid; aliphatic C$_{1-20}$ carboxylic acids, such as 2-ethylhexylcarboxylic acid, aliphatic perfluorocarboxylic acids, such as trifluoroacetic acid and perfluorooctanoic acid; aliphatic dicarboxylic acids, such as oxalic acid and, aromatic, optionally C$_{1-20}$-alkyl-substituted sulfonic acids, such as benzenesulfonic acid, p-toluene-sulfonic acid and dodecyl benzenesulfonic acid. Specific examples of iron salts comprise at least one of FeCl$_3$, Fe$_2$(SO$_4$)$_3$, Fe(ClO$_4$)$_3$ and Fe$_2$(S$_2$O$_8$)$_3$. Other oxidants comprise at least one of H$_2$O$_2$, K$_2$Cr$_2$O$_7$, ammonium persulfate, potassium permanganate, copper tetrafluoroborate, iodine, air and oxygen.

While any suitable polyanion can be employed, examples of suitable polyanions comprise an anion of a polycarboxylic acid, such as polyacrylic acid, polymethacrylic acid, products that are commercially available as Nafion®, polymaleic acid, and polymeric sulfonic acids, such as polystyrene sulfonic acid and polyvinyl sulfonic acid. The polycarboxylic and polysulfonic acids may also be copolymers of vinyl carboxylic and vinyl sulfonic acids with other monomers, such as acrylates and styrene. The molecular weight of the acids supplying the polyanions is normally in the range from about 1,000 to about 500,000, typically from about 2000 to about 500,000 and typically about 200,000.

Monomers of the formula A lend themselves to metal-catalyzed polymerizations. Conditions can vary depending on the nature of the X and X' substituents.

One method suitable for preparing oligomers and polymers, such as, poly(2-pentafluorosulfanyl-thieno[3,4-b] thiophene), comprises an electrochemical process wherein 2-pentafluorosulfanyl-thieno[3,4-b]thiophene is polymerized in an electrochemical cell using a three electrode configuration. A suitable three electrode configuration comprises an ITO working electrode, a platinum flag counter electrode and an Ag/Ag+ non-aqueous reference electrode. While any suitable electrolyte can be employed, examples of suitable electrolytes comprise at least one member selected from the group consisting of tetrabutylammonium perchlorate/acetonitrile, lithium triflate/acetonitrile and tetrabutylammonium hexafluorophosphate/acetonitrile. Among the many solvents, acetonitrile is preferred due to its large electrochemical window (e.g., about −2.5V to about +2.5V), but other electrochemically stable solvents like DMF, DMSO, THF, among others, may be utilized if their electrochemical window is sufficiently wide. The concentration of the electrolyte is typically about 100 mM but concentrations as low as 1 mM and as high as 1 M may be utilized. The temperature is usually maintained at about room tempearture for convience, but may be raised or lowered to the limits of the solvent electrolyte system. The concentration of monomers can be as low as 1 mM and as high as 1 M. Electrochemical polymerizations can be carried out in an inert atmosphere, i.e. under a blanket of nitrogen or argon, or in some cases under atmospheric conditions. In order to obtain more reproducible results it is recommended to use deoxygenated anhydrous solvents, freshly recrystallized electrolytes, and monomers with the highpurity. The electrochemical polymerization should be run under a blanket of an inert solvent of in a highly controlled environment, i.e. drybox.

In some cases, thienothiophene oligomers and polymers may be doped with conventional p- and n-type dopants post polymerization of the respective monomers. The doping process may involvetreating the oligomer or polymer (e.g., semiconductor material film), with an oxidizing or a reducing agent in a redox reaction to form delocalized ionic centers in the material, with the corresponding counterions derived from the applied dopants. Doping methods may comprise for example exposure to a doping vapor in the atmospheric or at a reduced pressure, electrochemical doping in a solution containing a dopant, bringing the dopant in contact with the oligomer or polymer to be thermally diffused, and ion-implantantion of the dopant.

Conductive polymeric materials having holes (p-doped) may be formed via conventional p-dopants which can comprise halogen atoms, e.g., I2, Cl2, Br2, ICl, ICl3, IBr and IF, Lewis acids, e.g., PF5, AsF5, SbF5, BF3, BCl3, SbCl 5, BBr3 and SO3, protonic acids, organic acids, or amino acids, e.g., HF, HCl, HNO3, H2SO4, HClO4, FSO3H and ClSO3H, transition metal compounds, e.g., FeCl3, Fe(OCl) 3, Fe(ClO4)3, Fe(4-CH3C6H4SO3)3, TiCl4, ZrCl4, HfCl4, NbF5, NbCl5, TaCl5, MoF5, MoCl5, WF5, WCl6, UF6 and LnX3 wherein Ln is a lanthanoid and X is an anion, e.g., Cl—, Br—, I—, I3—, HSO 4-, SO42-, NO3-, ClO4-, BF4-, B12F122-, PF6-, AsF6-, SbF6-, FeCl4-, Fe(CN)63-, and anions of various sulfonic acids, such as aryl-SO3-. Also, O2, as well as O3 may be used.

Conductive polymeric materials employing electrons as carriers as in n-doped polymeric films may utilize conventional n-dopants which comprise the alkali metals (e.g., Li, Na, K, Rb, and Cs), alkaline-earth metals (e.g., Ca, Sr, and Ba).

The 2-pentafluorosulfanyl-thieno[3,4-b]thiophene monomer and its derivatives can be copolymerized with other polymerizable monomers capable of forming electrically conductive polymers. Such monomers comprise at least one member selected from the group consisting of benzo- and bisbenzothiophenes, thienothiophenes, thiophenes, dithienothiophenes, pyridylthiophenes, substituted thiophenes, substituted thieno[3,4-b]thiophenes, dithieno[3,4-b:3',4'-d] thiophene, pyrroles, bithiophenes, substituted pyrroles, phenylene, substituted phenylenes, naphthalene, substituted naphthalenes, biphenyl and terphenyl and their substituted versions, phenylene vinylene and substituted phenylene vinylene. Other monomers are described in U.S. Pat. No. 4,959,430, and U.S. Pat. No. 4,910,645; these patents and such monomers are incorporated by reference.

In processing oligomers and polymers of 2-pentafluorosulfanyl-thieno[3,4-b]thiophene and derivatives, additives such as at least one member selected from the group consisting of ethylene glycol, diethylene glycol, mannitol, propylene 1,3-glycol, butane 1,4-glycol, N-methylpyrrolidone, sorbitol, glycerol, propylene carbonate and other appropriate high boiling organics can be added to dispersions to improve conductivity of the films prepared from these dispersions The amount of additive can vary but normally is in the range of about 0.1 wt % to about 30 wt %. Other common additives for tailoring electrically conductive polymers can be employed as desired and can comprise at least one member selected from the group consisting of antioxidants, UV stabilizers, surfactants, and conductive fillers such as particulate copper, silver, nickel, aluminum, carbon black, mixtures thereof, among others. Non-conductive fillers such as at least one member selected from the group consisting of talc, mica, wollastonite, silica, clay, TiO2, dyes, pigments, mixtures thereof, among others,can also be incorporated to promote specific properties such as increased modulus, surface hardness, surface color and the like.

The following examples are provided to illustrate various embodiments and comparisons and are not intended to restrict the scope of the invention.

EXAMPLE 1

Production of
2-pentafluorosulfanyl-thieno[3,4-b]thiophene
(2-SF$_5$-TT)

The purpose of this example is to provide a representative five step route to produce the monomer 2-pentafluorosulfanyl-thieno[3,4-b]thiophene (2-SF$_5$-TT) having the formula:

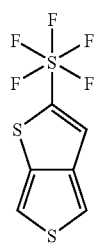

Step 1 Formation of
3-bromo-4-(trimethylsilylethynyl)thiophene

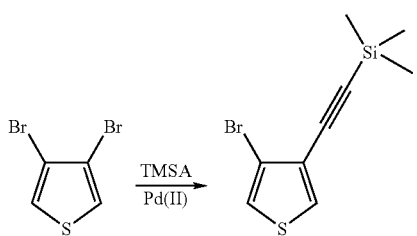

A 2-liter round-bottomed, three-necked flask was equipped with a reflux condenser, a mechanical stirrer, and a thermocouple, then purged with dry nitrogen gas. The flask was then charged with 240 g diethylamine (previously dried over KOH pellets and filtered), 387.04 g (1.60 mol.) 3,4-dibromothiophene, 800 mg (3.04 mmol) triphenylphosphine, 600 mg (5.48 mmol) copper(I)iodide, and 78.56 g (0.80 mol.) trimethylsilylacetylene. The stirred mixture was warmed to 40° C. 2.00 g (2.8 mmol.) of dichlorobis(triphenylphosphine)palladium(II) was then added. The reaction was maintained at 40° C. for 4 hrs with mechanical stirring and a static nitrogen blanket. At that point the reaction mixture was deemed complete and the reaction mixture was cooled to room temperature.

Recovery of the product, 3-bromo-4-(trimethylsilylethynyl)thiophene, was effected by placing the reaction mixture on a roto-evaporator and the diethylamine was removed by evaporation. 600 mL of pentane was added to the residual from evaporation along with 40 g of activated carbon (Darco, 12–20 mesh). The pentane solution was then filtered through a silica gel column (100 g) to remove palladium, followed by 600 mL or more of pentane. The pentane solvent from the collected solution was removed via evaporation on a roto-evaporator. Mass of isolated crude product was approximately 316 g. The residual material was vacuum distilled and 3-bromo-4-(trimethylsilylethynyl)thiophene recovered. The product was analyzed by NMR spectroscopy and the following results were obtained: $^1$H-NMR: δ (ppm) 0.3 (s), 7.19, 7.45; $^{13}$C-NMR: δ (ppm) −0.1, 97, 113, 122, 123, 129.

Step 2 Formation of 3-bromo-4-ethynylthiophene

The product of step one was converted to 3-bromo-4-ethynylthiophene according to the equation as follows:

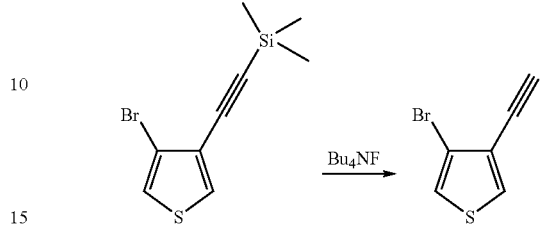

3-Bromo-4-(trimethylsilylethynyl)thiophene (10 g,38 mmol) and THF (45 mL) was stirred and cooled to −5° C. Tetrabutylammonium fluoride (40 mL 1M in THF) was added slowly maintaining the temperature −5° to 0° C. The reaction was stirred for 30 minutes after the addition of the tetrabutylammonium fluoride was complete. Water (100 mL) was added to the flask and the product extracted with pentane. The THF layer was washed with dilute HCl then water and finally dried over magnesium sulfate. The product was recovered as an orange liquid after the solvent was removed by rotary evaporation. The yield of 3--bromo-4-ethynylthiophene was 92%. Bp 58° C., 1.5 mm Hg. The product was analyzed by NMR spectroscopy and the following results were obtained: $^1$H-NMR: δ (ppm) 7.4, 7.5, 7.7; $^{13}$C-NMR: δ (ppm) 77, 82, 114, 124, 125, 134.

Step 3 Formation of 3-Bromo-4-(1-bromo-2-pentafluorosulfanyl-vinyl)-thiophene

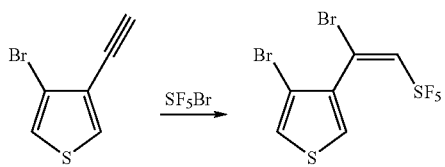

3-Bromo-4-ethynylthiophene (7.3 g, 39 mmol), pentane (130 mL) and potassium fluoride (0.38 g) were charged to a stainless steel Parr reactor. The solution was cooled to −50° C. and degassed. Pentafluorosulfur bromide (42 mmol) was condensed into the solution at −50° C. and stirred for one hour (alternatively pentaflurorsulfur chloride may be used). The cooling bath then was removed and the reaction stirred an additional hour. The resulting solution was treated with cold aqueous sodium bicarbonate. The aqueous layer was separated from the pentane/product layer and the pentane/product layer was dried over magnesium sulfate to yield the desired product. The product was analyzed by NMR spectroscopy and the following results were obtained: $^1$H-NMR: δ (ppm) 7.1 (pent,1H), 7.3 (d 1H), 7.4 (d,1H); $^{19}$F-NMR: δ (ppm) 66 (d, 4F), 80 (pent, 1F); MS: m/z 396, 394, 392, 317, 315, 269, 267, 265, 243, 241, 207, 205, 188, 186, 126, 89, 81, 63.

Step 4 Formation of 3-bromo-4-(pentafluorosulfanylethynyl)thiophene

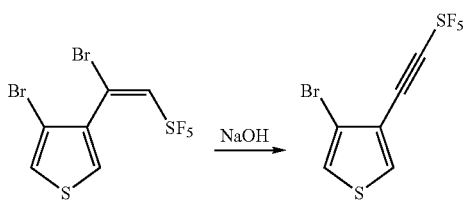

The product, 3-bromo-4-(pentafluorsulfanylethynyl) thiophene, was formed by HBr elimination. Sodium hydroxide powder (6 g, 150 mmol) was added to the pentane/product solution and stirred at room temperature. When HBr elimination was complete, the solution was filtered to remove the base and solvent was removed by rotary evaporation. The product, 3-bromo-4-(pentafluorosulfanylethynyl)thiophene, was recovered as a yellow liquid in 78% yield. It may be purified by distillation at 55° C./200 mTorr. The product was analyzed by NMR spectroscopy and the following results were obtained: $^1$H-NMR; δ (ppm) 7.3 (d 1H), 7.8 (d, 1H); $^{19}$F-NMR; δ (ppm) 76 (pent, 1F), 83 (d, 4F); MS: m/z 316, 314, 294, 206, 204, 215,106, 89, 81, 61.

Step 5 Formation of 2-pentafluorosulfanyl-thieno[3,4-b]thiophene

The product of step four was converted to pentafluorosulfanyl-thieno[3,4-b]thiophene according to the equation as follows

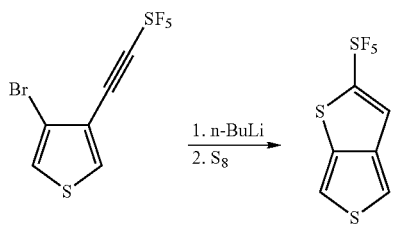

A mixture of 100 ml of diethyl ether and 8.38 g of 3-bromo-4-(pentafluorsulfanylethynyl)thiophene (0.0268 mol) was placed in a 250 mL round-bottomed, three-necked flask equipped with a thermometer-gas inlet combination, a magnetic stir bar, a gas outlet, and a septum sealed port. The air in the flask was completely replaced by nitrogen, after which the solution was cooled to −78° C. (bath with dry ice/acetone).

A solution of a 12.8 mL of 2.5 Molar n-BuLi (0.032 mol, 20% excess) in hexane was added over a few minutes by syringe through the septum, while keeping the temperature below −70° C. Fifteen minutes after completion of n-butyl lithium addition, and the reaction temperature maintained at −78° C., 0.875 g of dry, powdered sulfur (0.0273 mol., 2% excess) was added over a few seconds. The reaction was maintained in the bath and the temperature held below −70° C. After fifteen minutes, 100 mL of methanol, at approx −50° C. was added to the reaction mix and the reaction allowed to warm to room temperature over about 1 hr. The reaction mixture was maintained under nitrogen at 20–25° C. for 20 hr.

The mixture was recovered by filtering through Whatman #1 paper and the solvent removed by rotary evaporation (38° C.). Hexane (80 mL) was added to the flask in 5 aliquots, extracting liquid product from solid residue. The hexane solution was filtered through a 0.45 micron filter and, chromatographed under nitrogen on silica gel with hexane solvent. A forecut—defined to include the shoulder on the UV detectable main peak—and the heartcut—the main UV detected peak, were collected. Solvent was stripped from each cut by rotary evaporation (35° C.). Drying the heartcut at 0.5 torr at 20 C, yielded 2.61 g, purity 99.7%, of the monomer 2-pentafluorosulfanyl-thieno[3,4-b]thiophene.

To the concentrated forecut, 2 mL of hexane was added and the resulting solution cooled to −78° C. The mother liquor was removed from the solids. The solids were recrystallized by adding another 2 mL of hexane and repeating the procedure. Drying at 20° C. and 0.75 torr yielded 0.44 g of 99.8% purity 2-pentafluorosulfanyl-thieno[3,4-b]thiophene. (sum of isolated yield =43%). The product was analyzed by NMR spectroscopy and the following results were obtained: $^1$H-NMR: δ (ppm) 7.29, 7.4, 7.58; $^{13}$C-NMR: δ (ppm) 111, 117.2, 117.8, 134.2, 140.5, 157; $^{19}$F-NMR: δ (ppm) 69.5(d), 81 (pent);

EXAMPLE 2

Electrochemical Synthesis of Poly(2-pentafluorosulfanyl-thieno[3,4-b]thiophene)

2-Pentafluorosulfanyl-thieno[3,4-b]thiophene was dissolved in 100 mM tetrabutylammonium hexafluorophosphate/anhydrous acetonitrile solution to a concentration of 10 mM monomer and was electrochemically polymerized employing a 3-electrode configuration, using an ITO working electrode (1 cm$^2$ Delta Technologies, Limited, R$_s$=5–15 Ohm, CG-501N—CUV), platinum flag counter electrode (1 cm$^2$), and a Ag/Ag+nonaqueous reference electrode. The reference electrode (Bioanalytical Systems, Inc.; MF-2062) consisted of a Ag wire in a 0.1 M AgNO$_3$ anhydrous acetonitrile solution. A CH Intruments Model 700B Series Electrochemical Analyzer/Workstation was utilized to drive the electrochemical polymerization at room temperature under a blanket of nitrogen. The applied potential was cycled between 1.6 V and 0 V at a rate of 100 mwsec.

Polymerization was apparent from the development of a blue film on the surface of the transparent ITO electrode.

EXAMPLE 3

Electrochemical Synthesis of Poly(2-pentafluorosulfanyl-thieno[3,4-b]thiophene)

2-Pentafluorosulfanyl-thieno[3,4-b]thiophene was dissolved in 100 mM tetrabutylammonium hexafluorophosphate/anhydrous acetonitrile solution to a concentration of 10 mM monomer and was electrochemically polymerized employing a 3-electrode configuration, using an ITO working electrode (1 cm$^2$, Delta Technologies, Limited, R$_s$=5–15 Ohm; CG-50IN-CUV), platinum flag counter electrode (1 cm$^2$), and a Ag/Ag+ nonaqueous reference electrode. The reference electrode (Bioanalytical Systems, Inc.; MF-2062) consisted of a Ag wire in a 0.1 M AgNO$_3$ anhydrous acetonitrile solution. A CH Intruments Model 700B Series Electrochemical Analyzer/Workstation was utilized to drive the electrochemical polymerization at room temperature under a blanket of nitrogen. The applied potential was kept constant at 1.3V for 30 seconds.

Polymerization was apparent from the development of a blue film on the surface of the transparent ITO electrode.

The invention has been described with reference to particular embodiments, but other embodiments are apparent to persons of skill in the art, and are included within the scope of the claims.

The invention claimed is:

1. A monomer represented by the formula comprising:

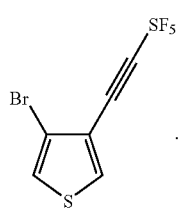

2. A monomer represented by the formula comprising:

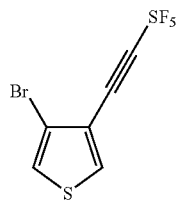

obtained by a reaction comprising contacting sodium hydroxide with a monomer represented by the formula comprising:

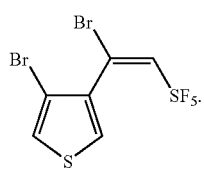

3. The monomer of claim 2 wherein the reaction is conducted in the presence of at least one solvent.

4. The monomer of claim 3 wherein the solvent comprises at least one member selected from the group consisting of hydrocarbons, ethers, halocarbons, alcohols and water.

* * * * *